(12) United States Patent
Davenport et al.

(10) Patent No.: US 9,381,096 B2
(45) Date of Patent: Jul. 5, 2016

(54) METHOD AND APPARATUS TO IDENTIFY COORDINATED COMPONENTS

(71) Applicant: Biomet Manufacturing, LLC, Warsaw, IN (US)

(72) Inventors: Austen Davenport, Columbia City, IN (US); Tyler D. Witt, Warsaw, IN (US); Seth Nash, Columbia City, IN (US); W. Jason Slone, Silver Lake, IN (US); Nikie Becknell, Leesburg, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 65 days.

(21) Appl. No.: 14/025,941

(22) Filed: Sep. 13, 2013

(65) Prior Publication Data
US 2014/0074249 A1    Mar. 13, 2014

Related U.S. Application Data

(60) Provisional application No. 61/700,581, filed on Sep. 13, 2012.

(51) Int. Cl.
*A61F 2/32* (2006.01)
*A61F 2/46* (2006.01)
*A61F 2/34* (2006.01)
*A61F 2/30* (2006.01)

(52) U.S. Cl.
CPC .............. *A61F 2/4609* (2013.01); *A61F 2/34* (2013.01); *A61F 2002/30616* (2013.01); *A61F 2002/30713* (2013.01)

(58) Field of Classification Search
CPC ... A61F 2/34; A61F 2/46; A61F 2002/30713; A61F 2002/30616; A61F 2002/4684
See application file for complete search history.

(56) References Cited

U.S. PATENT DOCUMENTS

| | | | |
|---|---|---|---|
| 2,270,188 A | | 1/1942 | Longfellow |
| 5,156,626 A | * | 10/1992 | Broderick et al. ......... 623/22.12 |
| 5,192,282 A | | 3/1993 | Draenert et al. |
| 5,336,240 A | | 8/1994 | Metzler et al. |
| 5,364,400 A | | 11/1994 | Rego, Jr. et al. |
| 5,397,356 A | | 3/1995 | Goble et al. |
| 5,464,427 A | | 11/1995 | Curtis et al. |
| 5,562,671 A | | 10/1996 | Goble et al. |
| 5,597,384 A | * | 1/1997 | Walker ................. A61F 2/0095 206/459.5 |
| 5,674,224 A | | 10/1997 | Howell et al. |
| 5,895,425 A | | 4/1999 | Grafton et al. |
| 6,056,749 A | | 5/2000 | Kuslich |
| 6,132,433 A | | 10/2000 | Whelan |
| 6,132,442 A | | 10/2000 | Ferragamo et al. |
| 6,210,376 B1 | | 4/2001 | Grayson |
| 6,214,012 B1 | | 4/2001 | Karpman et al. |
| 6,306,138 B1 | | 10/2001 | Clark et al. |
| 6,368,322 B1 | | 4/2002 | Luks et al. |
| 6,471,707 B1 | | 10/2002 | Miller et al. |

(Continued)

OTHER PUBLICATIONS

Acetabular Reference Guide, DJO Surgical, Encore Medical, L.P.; 17 pages (2008).

*Primary Examiner* — Brian Dukert
(74) *Attorney, Agent, or Firm* — Schwegman Lundberg & Woessner, P.A.

(57) ABSTRACT

A prosthetic system is disclosed that can have a feature for identifying an aspect of the prosthetic member and related instruments. The identification feature can identify cooperating components of the prosthetic system, such as an implant and instruments for use with the implant.

11 Claims, 3 Drawing Sheets

(56) References Cited

U.S. PATENT DOCUMENTS

| | | |
|---|---|---|
| 6,565,572 B2 | 5/2003 | Chappius |
| 6,623,524 B2 | 9/2003 | Schmieding |
| 6,752,830 B1 | 6/2004 | Goble et al. |
| 2001/0053934 A1 | 12/2001 | Schmieding |
| 2002/0058941 A1 | 5/2002 | Clark et al. |
| 2002/0087160 A1 | 7/2002 | Clark et al. |
| 2009/0099664 A1* | 4/2009 | Forrester .................. 623/21.18 |

* cited by examiner

METHOD AND APPARATUS TO IDENTIFY COORDINATED COMPONENTS

CROSS-REFERENCE TO RELATED APPLICATIONS

This application claims the benefit of U.S. Provisional Application No. 61/700,581, filed on Sep. 13, 2012, entitled METHOD AND APPARATUS TO IDENTIFY COORDINATED COMPONENTS. The entire disclosure of the above application is incorporated herein by reference.

FIELD

The subject application is related to prostheses and instruments for a procedure to implant prostheses, and particularly to determining a correlation between related prosthetic implants and tools.

BACKGROUND

This section provides background information related to the present disclosure which is not necessarily prior art.

During a surgical procedure a set of instruments may be used to perform a procedure. The instruments can include implantation instruments, reaming instruments, trial instruments, and other selected instruments for a procedure. Each of the instruments can be related to a selected size of prosthesis. For example, a 50 mm prosthetic acetabular implant may be designed to coordinate with a similarly sized reaming instrument for preparing an acetabulum for implantation of the acetabular prosthesis. Accordingly, it is desirable to use a related size instrument for a selected and specific prosthetic member.

SUMMARY

This section provides a general summary of the disclosure, and is not a comprehensive disclosure of its full scope or all of its features.

A prosthesis type (i.e. acetabular prosthesis, femoral head, etc.) can be provided and made in various different sizes. Each size of prosthesis can have instruments that are coordinated in size for implantation and preparation of an anatomy for implantation of the prosthesis. The different sizes of the prosthesis, therefore, can require different size instrument systems. The instrument systems can be used and/or selected intra-operatively or preoperatively based upon a selected patient. For example, a prosthetic acetabular cup can be provided in various external diameters, such as 50 mm, 60 mm, 70 mm, or other appropriate external diameters. Related instruments can include a reamer for reaming an acetabulum to prepare the acetabulum for implantation of the acetabular prosthesis. Selecting the correct and coordinated size instrument can be useful and important to increase selected results of a prosthesis.

Accordingly, it may be desirable to increase efficiency and speed of a procedure by uniquely identifying those instruments that relate to a specific prosthetic member (e.g. based on size of the prosthetic member). For example, a reamer and a prosthetic acetabular cup can be provided in an identical or substantially identical color for ease of identification and relation/coordination between the selected prosthetic member and the related instrument. The instrument may be for implanting the selected prosthetic member. For example, a 50 mm acetabular prosthetic cup can be colored blue and a reamer for reaming an acetabulum to prepare it for the acetabular cup can also be colored blue. Similarly, other prosthetic members and related/coordinated instruments can be color coded in substantially identical or similar colors including red, orange, green, and other colors. Additionally, other portions of a prosthetic assembly, including a liner, trial shells, trial liners, trial femoral heads, femoral head, and the like can be similarly colored to match based upon size and configuration. Additionally, other prosthetic assemblies can be color coded to identify related sizes, such as a distal femur or proximal tibial prosthesis for a knee prosthetic system or other selected prosthetic systems.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
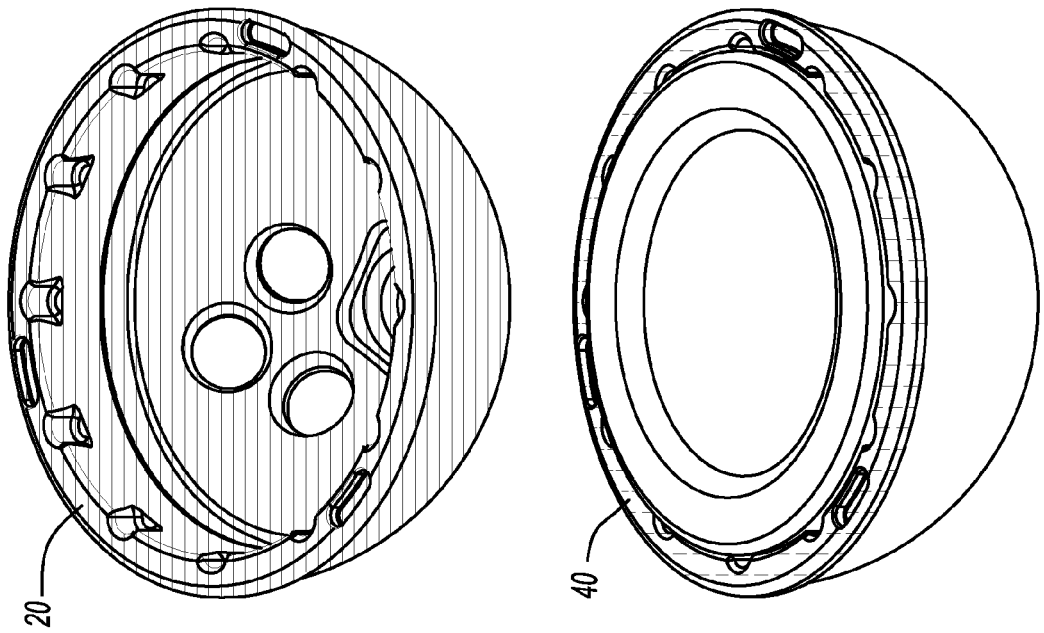
FIG. 1 is a perspective view of various prostheses with color coding.
Figure 1:
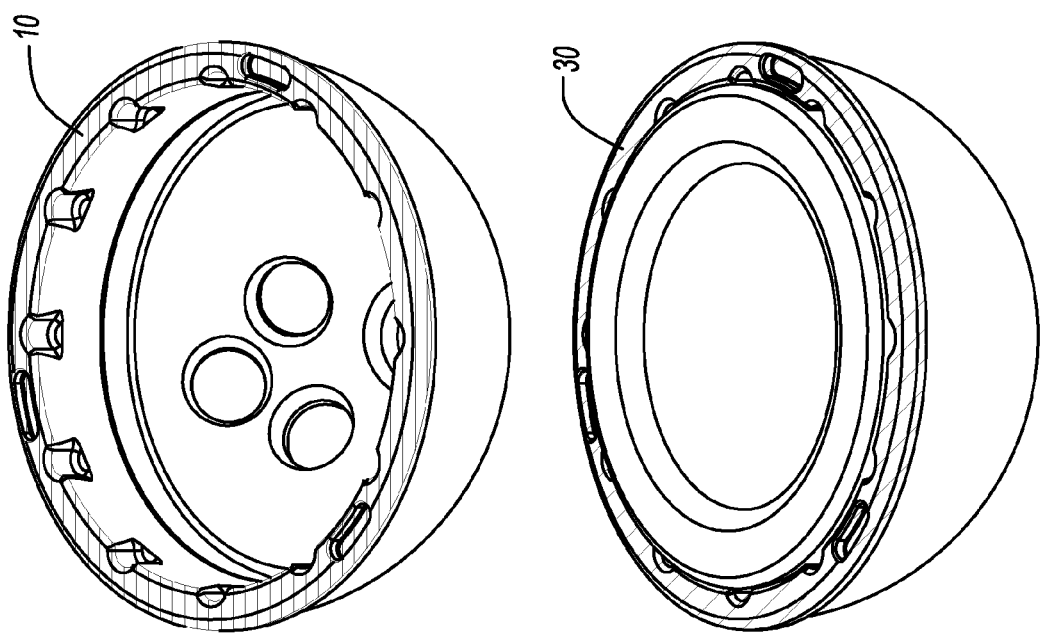

Example embodiments will now be described more fully with reference to the accompanying drawings.

In a prosthetic system, such as a total hip replacement arthroplasty (THA) prosthesis, a knee replacement prosthesis, a shoulder replacement prosthesis (including a humeral head prosthesis or a glenoid prosthesis). The various components of the various prosthetic systems can be coded to identify their respective coordination instruments. The prosthetic systems, in addition to the prostheses, can include related instruments, such as reaming instruments or trial instruments. For example, a trial acetabular prosthesis, a trial acetabular cup, and trial liner may be used to ensure appropriate sizing and joint replacement in a patient. Additionally, various instruments including reamers and resection tools can be used to resect selected portions of the acetabulum. For example, an acetabular reamer can be provided to ream an acetabulum to prepare it for an acetabular prosthesis.

The various instrument sets and prosthetic members can be coded to identify their respective coordinating portions. For example, a selected size acetabular prosthesis can be marked with a selected code or colored with a selected color and each of the instruments that relates to that size prosthesis can be included with the same color. For example, a trial shell, a prosthetic shell, and a reamer all of the same size can be colored a similar or identical color. Additionally, or as an alternative to the coloring, markings can be laser etched on to the various components.

Coloring of the prosthetic components and the instruments can be performed by anodizing the components. For example, a trial shell, a prosthetic shell, and a reamer can all be formed of a substantially similar material. For example, titanium can be used to form all of the components. It is also understood, however, that various other materials can be used to form the components, such as steel (including various stainless steels) and other metal or metal alloys for forming the trial and/or the reaming components. Each of the components can be colored with a substantially identical color, such as by anodizing the metal material. A polymer can also be colored a substantially identical color, such as a polymer liner for the acetabular prosthesis. The colors can be provided of substantially biocompatible components or coloring agents to ensure biocompatibility of the prosthetic members and the instruments. For example, anodizing titanium is substantially biologically inert.

Any selected portion of the various components can be color coded. Different portions of the instruments or the prosthetic members can be anodized. For example, only an exterior or superior rim can be color coded, such as anodizing, to minimize possible wear surfaces of the coloring component or ease of manufacturing.

Color coding the selected sizes, can be used to mitigate and substantially eliminate the possibility of non-matching components being mated during a procedure or used for preparing a patient for an implantation. For example, a prosthetic member that is made to mate with a selected size mating member can have micromotion (e.g. relative motion between at least two members generally in the range of about 0.0001 millimeters to about 1 mm) or movement after implantation if the appropriate size is not mated with the appropriate prosthetic member. Additionally, a prosthetic member that is formed to engage the anatomy after preparation in a particular manner can also have motion if the anatomy is not properly prepared with the selected size instrument. Accordingly, ensuring substantially proper mating of various components can reduce motion and wear, such as fretting, after implantation. The color coding can ensure and also provide a visual check to ensure that appropriately matched components are inserted/implanted and mated together.

When anodizing a component, an entire component can be anodized. Subsequent machining, such as during the manufacturing process, can ensure that only selected portions of the prosthetic member or instrument includes the selected coloring. For example, an entire surface of a prosthetic shell can include an anodized coloring, but machining of the interior of the prosthetic member can remove the interior coloring of the prosthetic member. By removing the color on the interior portion possible wear or removal of the color may also be substantially minimized or reduced.

Additionally, it is understood that a plurality of colors may be included on the single prosthetic member. For example, a primary or main color can identify a size while a secondary color can be used to identify an additional feature of the prosthetic member or component. Additional or secondary features can include locking features, location of a removal feature, hole orientation (e.g. screwhole orientation), and other appropriate features. For example, a secondary color can be used to identify a RINGLOC® locking feature of a prosthetic member. A liner including the mating feature can also have a primary and secondary color to ensure that it is the proper size and includes the appropriate locking feature.

Hole orientation can include orientation of screwholes for fixing a prosthesis to the anatomy. For example, acetabular prostheses can include screwholes to allow for passage of a screw intro a pelvis. Other prosthetic members, such as intramedullary (IM) rods can include through screwholes that can have screws that pass therethrough. Orientation and position of the screwholes can be identified with a secondary color, such as spacing between screwholes and distance of a first screwhole from a terminal end of the IM can be identified by a color for ease of identification once positioned within the anatomy.

According to various embodiments, as illustrated in FIG. 1, an acetabular prosthesis can be included or provided with a plurality of colors. For example, a blue rimmed prosthesis 10 can have a coloring around an upper or outer rim. According to various embodiments, however, an entirely blue acetabular prosthesis 20 can be provided where the entire acetabular prosthesis 20 can be colored the same color. As discussed above, however, during manufacturing various portions of the acetabular prosthesis may be machined away or covered, thus creating only an upper rim that is colored, as illustrated in the prosthesis 10. As discussed above in addition, however, a plurality of colors can be provided to indicate the different sizes or features of prostheses. For example, a green upper rim prosthesis 30 and a purple upper rim prosthesis 40 are illustrated as exemplary prosthesis members. Again, it is understood that any appropriate prosthesis, such as a hip stem, a femoral head, a knee replacement (e.g., a distal femoral component and a proximal tibia component) can all be provided where different colors can indicate different sizes and features.

Figure 2:
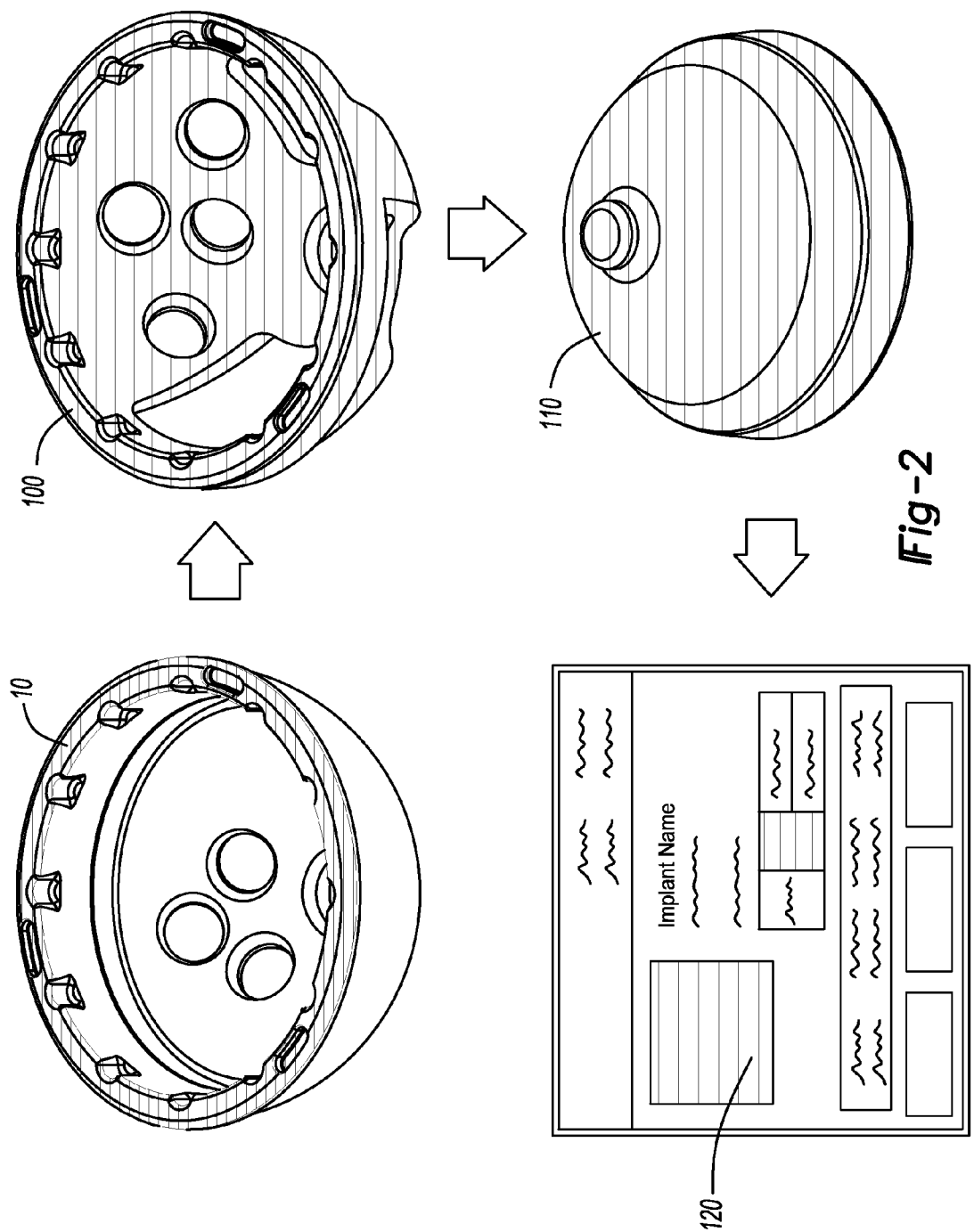
FIG. 2 is a schematic view of a prosthesis and selected instruments including a similar color code.

With reference to FIG. 2, all of the components that relate to a single size or feature can be provided in the same color. As illustrated in FIG. 2, the prosthesis 10 can include a blue color in the upper rim area. Therefore, a provisional member (which may also be a reamer or other instrument) 100 can also be blue. Further, a prosthetic liner or trial liner 110 may also be blue to identify that the components are configured to work with the same color coded prosthesis 10. In addition, packaging can include a blue colored label 120 that includes at least blue portions to identify the prosthetic members or instrument portions therein relate to a similarly colored selected size. It is further understood that the prosthetic members for the instruments, such as the provisional member 100 or the trial liner 110, can also be marked with other alphanumeric indications for identification of size, features, etc. In addition, it is understood that implant portions can also be provided in a similar color, such as actual implant liner in addition to the trial implant liner 110 and other instrument members such as other reamers and screws can also be provided in the same color to identify coordination with a similarly colored prosthesis.

Figure 3:
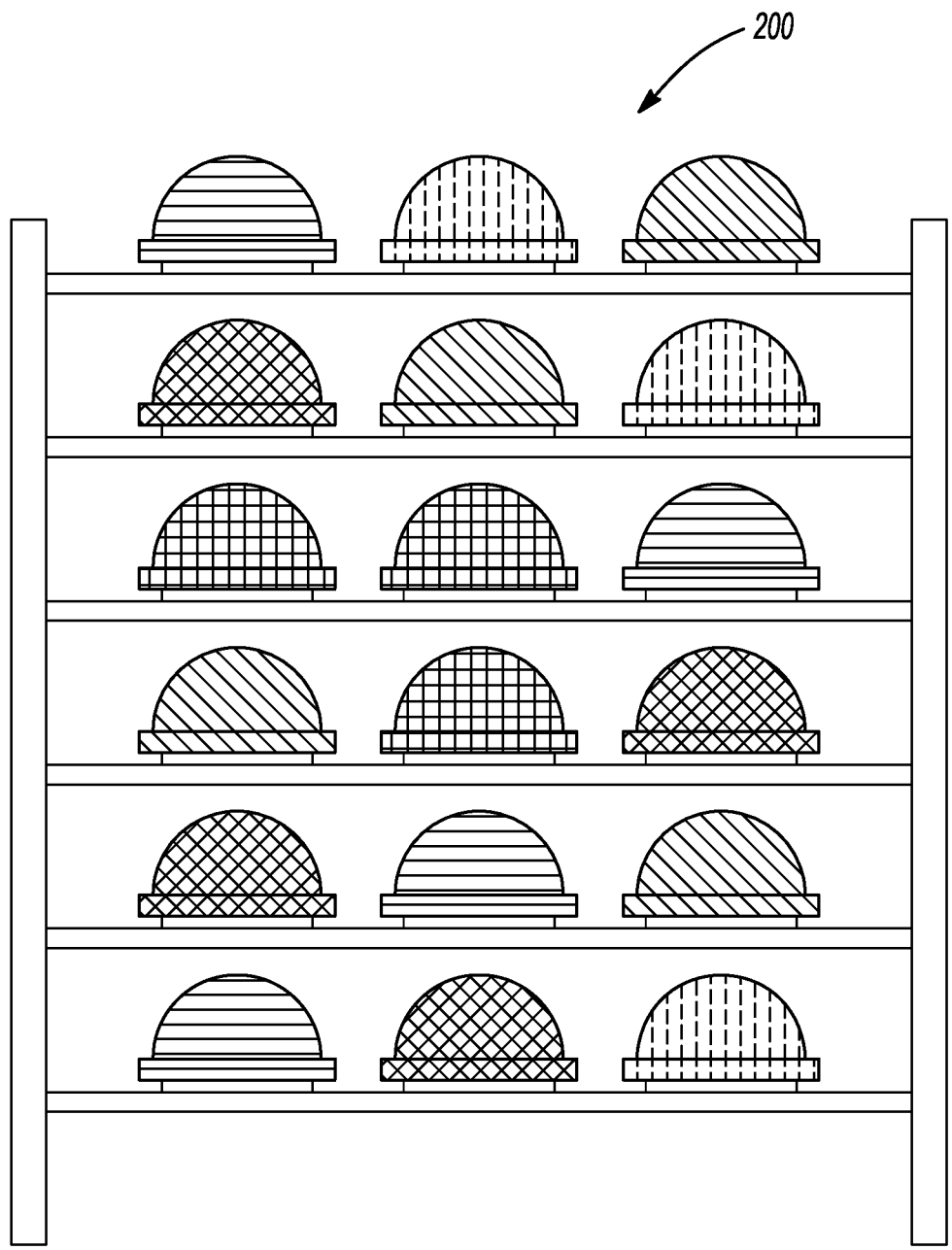
FIG. 3 is an illustration of a plurality of differently color coded prostheses and instruments.

Finally, with reference to FIG. 3, an implant system or kit 200 can be provided including a plurality of implant members in different colors. Each of the implant members' different colors can include different features or sizes, as discussed above. The kit 200 can be provided to allow selection by a user, such as a surgeon, during a procedure. In addition, it is understood, that a surgeon can identify a particular size or feature prior to beginning a procedure, such as a prosthetic implantation procedure. Nevertheless, during a procedure a surgeon can select a prosthesis from a prosthetic system or kit that includes a plurality of sizes. Once a surgeon has selected a specific size, the instruments that match in identification code, such as color, of the selected prosthetic member can then be used for the procedure providing a substantially immediate and obvious indication of compatibility of the various components.

Accordingly, it is understood that various prosthetic members, including acetabular prosthetic cups and liners, can be provided or colored with a selected color, such as through anodizing, for identification of coordinating and mating members. The instruments that coordinate or cooperate with the prosthesis can be provided in a substantially similar color or identical color as the implantable prosthesis for easy and efficient identification and matching of selected and coordinated components. Thus, the instruments for use with a selected size can be provided in the same color, or other identifying feature, as the actual prosthetic member for implantation.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A prosthetic assembly system, comprising:
  a prosthetic member configured to be implanted in a natural anatomy to replace a portion of the natural anatomy being provided with a first identification feature, wherein the first identification feature is one of a color and an alphanumeric marking, the prosthetic member includes a second identification feature, wherein the second identification feature is one of a color and an alphanumeric marking, wherein the second identification feature is different than the first identification feature;
  a first instrument operable to assist in implantation of the prosthetic member in a selected portion of the natural anatomy provided with the first identification feature;
  a second prosthetic member including both the first identification feature and the second identification feature;
  a third prosthetic member configured to be implanted in the natural anatomy to replace the portion of the natural anatomy being provided with a third identification feature different from the first identification feature and to distinguish the first prosthetic member from the third prosthetic member; and
  a second instrument operable to assist in implantation of the third prosthetic member in a selected portion of the natural anatomy provided with the third identification feature;
  wherein the first identification feature is configured to identify a matching coordination of the prosthetic member and the first instrument for performing a procedure and the third identification feature is configured to identify a matching coordination of the third prosthetic member and the second instrument for performing a procedure.

2. The system of claim 1, wherein the first instrument is at least one of a reamer, a liner provisional, a shell provisional, a face plate, or an inserter.

3. The system of claim 1, wherein the first identification feature is a color.

4. The system of claim 1, wherein the first identification feature is an anodized color formed on at least one of the prosthetic member or the first instrument.

5. The system of claim 1, wherein the first identification feature identifies at least a size of the prosthetic member and the second identification feature identifies at least one of a locking feature, a location of a removal feature, a hole orientation.

6. A prosthesis system, comprising:
  a first prosthetic member having a first identification code, wherein the first identification code is one of a color and an alphanumeric marking, the first prosthetic member having a second identification code, wherein the second identification code is one of a color and an alphanumeric marking, wherein the second identification code is different than the first identification code;
  at least one first instrument including a first reaming instrument or a first trial instrument including the first identification code and the second identification code;
  a second prosthetic member having a third identification code different from the first and second identification codes and to distinguish the first prosthetic member from the second prosthetic member; and
  a second instrument operable to assist in implantation of the second prosthetic member in a selected portion of a natural anatomy provided with the third identification code;
  wherein the first prosthesis member and the at least one first instrument are configured to coordinate matching for implantation of the first prosthetic member into a patient, and the third identification code is configured to identify a matching coordination of the second prosthetic member and the second instrument for performing a procedure.

7. The system of claim 6, wherein the at least one first instrument includes at least one of a first trial acetabular prosthesis, a first trial acetabular cup, and a first trial liner configured to ensure appropriate sizing for a joint replacement in a patient.

8. The system of claim 6,
  wherein the first prosthetic member is an acetabular prosthesis;
  wherein the at least one first instrument including a first reaming instrument includes an acetabular reamer configured to resect selected portions of an acetabulum of the patient for the acetabular prosthesis.

9. The system of claim 8, wherein the first identification code is a color.

10. The system of claim 8, further comprising:
  a first liner;
  wherein the first liner includes the first identification code and the second identification code.

11. The system of claim 10, wherein the first identification code identifies at least a size of the acetabular prosthesis and the first liner and the second identification code identifies at least one of a locking feature, a location of a removal feature, or a hole orientation.

\* \* \* \* \*